(12) United States Patent
Chon

(10) Patent No.: US 6,602,193 B2
(45) Date of Patent: *Aug. 5, 2003

(54) ULTRASOUND HANDPIECE

(75) Inventor: James Y. Chon, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/153,056

(22) Filed: May 22, 2002

(65) Prior Publication Data

US 2002/0138080 A1 Sep. 26, 2002

Related U.S. Application Data

(63) Continuation of application No. 09/625,294, filed on Jul. 25, 2000, now Pat. No. 6,478,766.

(51) Int. Cl.$^7$ .............................. A61B 8/00; A61B 17/20
(52) U.S. Cl. ...................... 600/439; 604/22; 600/446
(58) Field of Search ..................... 601/2, 13; 606/95, 606/159, 161, 169, 170, 171, 180; 600/459

(56) References Cited

U.S. PATENT DOCUMENTS

| 4,504,264 | A | 3/1985 | Kelman |
| 5,061,238 | A | 10/1991 | Shuler |
| 5,162,044 | A | 11/1992 | Gahn et al. |
| 5,222,959 | A | 6/1993 | Anis |
| 5,269,798 | A | 12/1993 | Winkler |
| 5,364,405 | A | 11/1994 | Zaleski |
| 5,453,087 | A | 9/1995 | Malinowski |
| 5,492,528 | A | 2/1996 | Anis |
| 5,505,693 | A | 4/1996 | Mackool |
| 5,617,866 | A | 4/1997 | Marian, Jr. |
| 5,681,986 | A | 10/1997 | Merk et al. |
| 5,722,945 | A | 3/1998 | Anis et al. |
| 5,730,718 | A | 3/1998 | Anis et al. |
| 5,797,848 | A | 8/1998 | Marian et al. |
| 5,827,292 | A | 10/1998 | Anis |
| 5,911,699 | A | 6/1999 | Anis et al. |
| 5,961,465 | A | 10/1999 | Kelly, Jr. et al. |
| 6,063,098 | A | 5/2000 | Houser et al. |
| 6,078,831 | A | 6/2000 | Belef et al. |
| 6,224,565 | B1 | 5/2001 | Cimino |

FOREIGN PATENT DOCUMENTS

EP        0 490 085 A1   6/1992

*Primary Examiner*—Marvin M. Lateef
*Assistant Examiner*—Runa Shah Qaderi
(74) *Attorney, Agent, or Firm*—Jeffrey S. Schira

(57) ABSTRACT

A handpiece having a set of longitudinally vibrating piezoelectric elements and which may additionally have an electric motor to provide rotational or oscillatory movement to the ultrasound horn. The piezoelectric elements are surrounded by a high temperature plastic sleeve, and the sleeve is filled with high temperature potting material. The potting material seal the piezoelectric elements against moisture without affecting the performance of the piezoelectric elements.

3 Claims, 3 Drawing Sheets

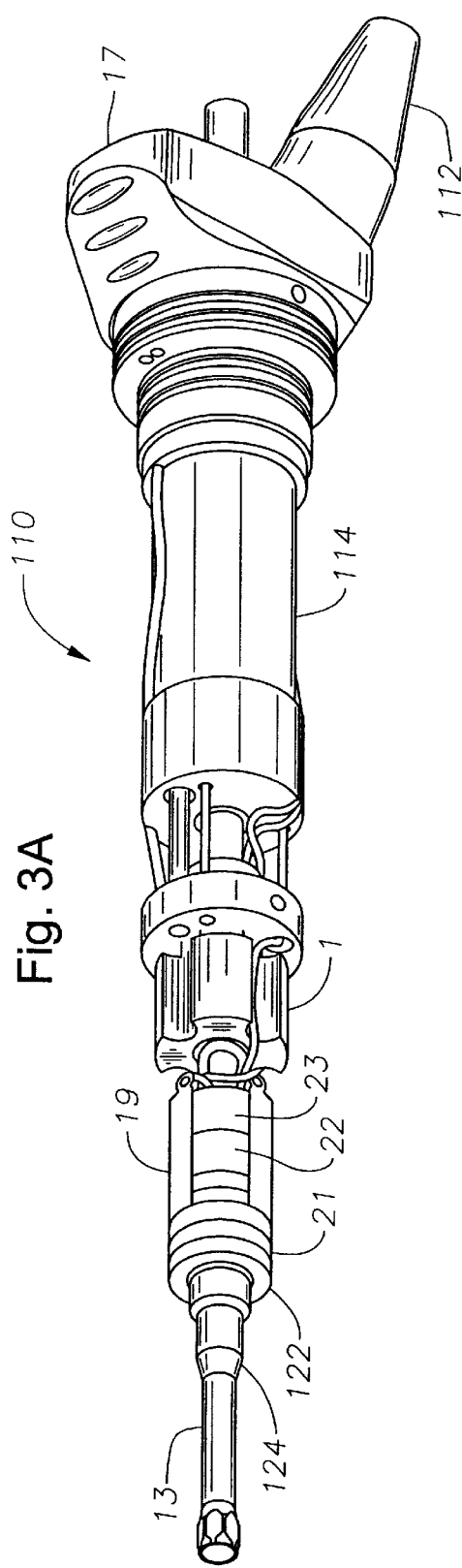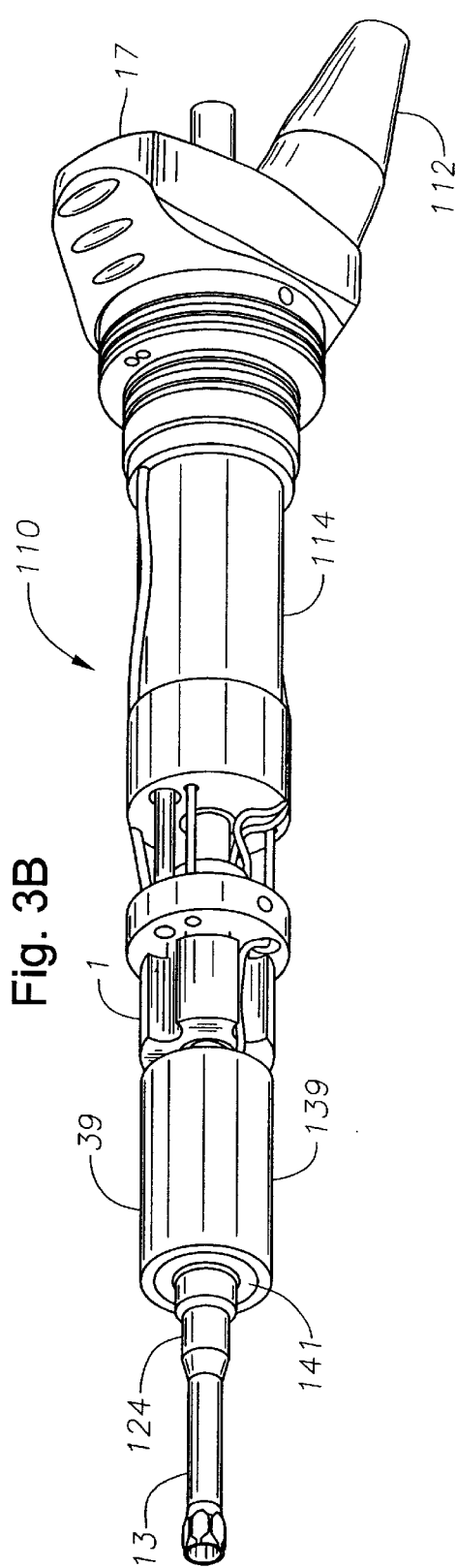

ULTRASOUND HANDPIECE

The application is a continuation of U.S. patent application Ser. No. 09/625,294, filed Jul. 25, 2000, now U.S. Pat. No. 6,478,766.

This invention relates to ultrasonic devices and more particularly to an ophthalmic phacoemulsification handpiece.

BACKGROUND OF THE INVENTION

A typical ultrasonic surgical device suitable for ophthalmic procedures consists of an ultrasonically driven handpiece, an attached hollow cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece at its nodal points by relatively inflexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

When used to perform phacoemulsification, the ends of the cutting tip and irrigating sleeve are inserted into a small incision of predetermined width in the cornea, sclera, or other location in the eye tissue in order to gain access to the anterior chamber of the eye. The cutting tip is ultrasonically vibrated along its longitudinal axis within the irrigating sleeve by the crystal-driven ultrasonic horn, thereby emulsifying upon contact the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the bore of the cutting tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the cutting tip.

Ultrasound handpieces are subjected to the extreme heat and pressure of autoclave sterilization, which can shorten the life of the piezoelectric elements. Prior attempts to increase the longevity of the electronic components of piezoelectric handpieces have been directed primarily to preventing moisture from entering the handpiece by better sealing of the outer shell and/or electric cabling. While these attempts have increased significantly the useful life of ultrasound handpieces, further improvements are needed.

Accordingly, a need continues to exist for an ultrasound handpiece having increased reliability.

BRIEF SUMMARY OF THE INVENTION

The present invention improves upon prior art ultrasonic devices by providing a handpiece having a set of longitudinally vibrating piezoelectric elements and which may additionally have an electric motor to provide rotational or oscillatory movement to the ultrasound horn. The piezoelectric elements are surrounded by a high temperature plastic sleeve, and the sleeve is filled with high temperature potting material. The potting material seal the piezoelectric elements against moisture without affecting the performance of the piezoelectric elements.

It is accordingly an object of the present invention to provide an ultrasound handpiece having both longitudinal and torsional motion.

It is a further object of the present invention to provide an ultrasound handpiece having piezoelectric elements sealed against moisture.

Another objective of the present invention is to provide a more reliable ultrasound handpiece.

Other objects, features and advantages of the present invention will become apparent with reference to the drawings, and the following description of the drawings and claims.

BRIEF DESCRIPTION OF THE DRAWINGS

FIGS. 3A & 3B are perspective views of one embodiment of the ultrasonic handpiece of the present invention having the inner and outer handpiece shells removed.

DETAILED DESCRIPTION OF THE INVENTION

Figure 1:
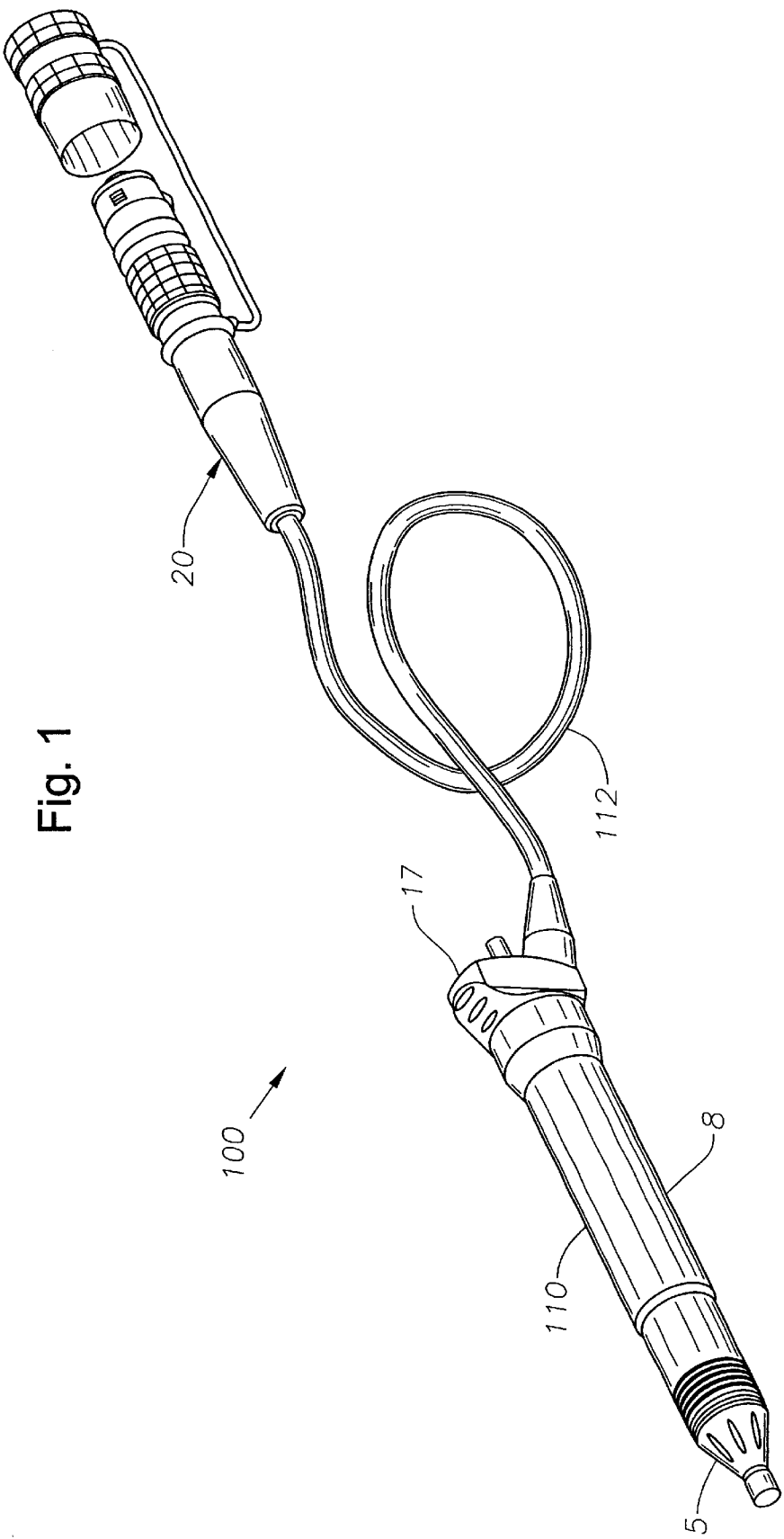
FIG. 1 is a perspective view of one embodiment of the ultrasonic handpiece of the present invention.

As best seen in FIG. 1, handpiece 100 of the present invention generally consists of handpiece body 110, electric cable 112 and electric connector 20. Handpiece 100 combines both longitudinal motion and rotary or oscillatory motion, such handpieces being more fully described in U.S. Pat. Nos. 5,222,959, 5,492,528, 5,827,292 (Anis), U.S. Pat. Nos. 5,722,945, 5,730,718, 5,911,699 (Anis, et al.) and U.S. Pat. No. 4,504,264 (Kelman), the entire contents of which are incorporated herein by reference. One skilled in the art will recognize that the present invention is suitable for use on ultrasonic handpieces having only longitudinal motion.

Figure 2:
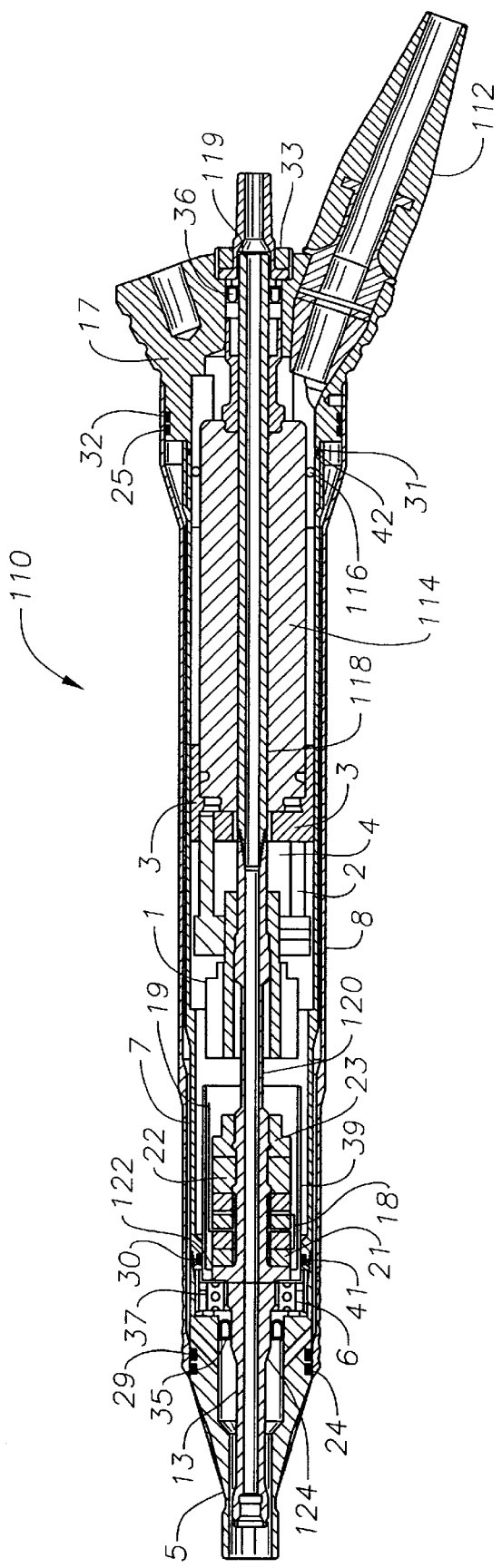
FIG. 2 is a cross-section view of one embodiment of the ultrasonic handpiece of the present invention.

As best seen in FIG. 2, handpiece body 110 of the present invention generally includes nosecone shell 5, handpiece inner shell 7, handpiece outer shell 8 and handpiece end piece 17. Motor 114 is mounted within inner shell 7 by motor mount 3 and seal 116 and may contain devices, such as torsioner ring 2 and torsioner wire 4, for limiting the rotary movement of motor 114. Attached to distal end of shaft 118 of motor 114 is driveshaft 120 portion of horn 13. Piezoelectric stack 21 is received over driveshaft 120 portion of horn 13 and held in place against end plate 122 on driveshaft 120 by split nuts 22 and 23. Front bulkhead 1 is threaded onto driveshaft 120 behind nut 23 to de-couple the ultrasonic energy generated by piezoelectric stack 21 from motor 114. Power is supplied to piezoelectric stack by electrodes 18 and 19, and the entire assembly may be surrounded by insulating sleeve 39. Ultrasound horn 13 is threaded into endplate 122 on driveshaft 120. Horn 13 is held within inner shell 7 by spring-loaded seal 35 and by bearing 37 contacting hub 124 of horn 13. Piezoelectric stack 21 is supported by bearings 6 and 41. Inner shell 7 is held within outer shell 8 by silicone rubber or elastomeric O-rings 30, 31, 41 and 42. Nosecone shell 5 is received in the distal end of outer shell 8 and sealed fluid tight by silicone rubber or elastomeric O-rings 24 and 29. End piece 17 is received on the proximal end of outer shell 8 and sealed fluid tight by silicone rubber or elastomeric O-rings 25 and 32. Proximal end 119 of motor shaft 118 is held within end piece 17 by spring-loaded seal 36 and by spanner ring 33.

In use, motor 114 is energized and causes motor shaft 118 to rotate. Rotation of shaft 118 causes rotation of driveshaft 120, piezoelectric stack 21 and horn 13. Rotation of horn 13 and motor shaft 118 causes friction and wear at the interface between hub 124 and seal 35 and distal end 119 of shaft 118 and seal 36. This friction can cause excessive wear on hub 124 and shaft 118, which preferably are made from titanium, by seals 35 and 36, which are preferably carbon/graphite filled, a very abrasive material. When such wear occurs, handpiece body 110 may no longer be sealed fluid tight, particularly in a steam autoclave. To prevent excessive wear on hub 124 and shaft 118, hub 124 and proximal end 119 of shaft 118 may be plated or coated with any hard coating such as titanium nitride, zirconium nitride, chromium nitride or boron carbide (also know as black diamond), but titanium nitride is preferred. While titanium nitride coatings may be applied as thin as 2–4 microns, the inventors have found that such a thin coating is easily cracked when applied over a relatively soft material such as titanium. Therefore, it has been discovered that a titanium nitride coating greater than 4 microns, and preferably between 9–12 microns gives the best results. Coatings greater than 4 microns, however, may change the surface morphology of the coating, resulting in a sandpaper-like finish undesirable for a sealing surface. The inventors have discovered that is such situations, polishing of the surface, for example, with a diamond powdered paste, removing approximately 1 micron of material or less, results in a satisfactory surface.

FIGS. 3A and 3B illustrate the operative parts of handpiece 110 with nosecone 5, inner shell 7 and outer shell 8 removed. As seen in FIG. 3A, endplate 122, piezoelectric stack 21, split nuts 22 and 23 and electrodes 18 and 19 are exposed to the atmosphere internal to handpiece 110. As been seen in FIG. 3B, piezoelectric stack 21, endplate 122 split nuts 22 and 23 and electrodes 18 and 19 may be covered by protective sleeve 39. Sleeve 39 preferably is made from a high temperature plastic such as polyetheretherketone (PEEK) and is slip-fitted around endplate 122, piezoelectric stack 21, split nuts 22 and 23 and electrodes 18 and 19. The interior of sleeve 39 may be filled with high temperature potting material 141, such as a primerless silicone adhesive (Dow Corning Q3-6611). The filling operation generally may include raising the temperature of potting material 141 and sleeve/piezoelectric stack assembly 139 to, for example, around 120° C. and injecting potting material 141 into sleeve/piezoelectric stack assembly 139 with a syringe. The elevated temperature is held for a short time, approximately 5 minutes, for example, to degas any air bubbles from potting material 141. Additional potting material 141 is injected into sleeve/piezoelectric stack assembly 139 to replace any volume lost by the escaping gases. The entire potting material 141 filled sleeve/piezoelectric stack assembly 139 is then cured, for example, at around 120° C. for 2 hours. Such a potting process does not affect the ultrasonic performance of handpiece 110, but helps to increase the reliability and longevity of handpiece 110 be sealing piezoelectric stack 21 and electrodes 18 and 19 from moisture.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. An ultrasound surgical handpiece, comprising:
   a) an outer shell;
   b) an ultrasound horn held within the shell;
   c) a piezoelectric element ultrasonically coupled to the horn;
   d) a sleeve surrounding the piezoelectric element; and
   e) a potting material within the sleeve sealing the piezoelectric stack from moisture so that the potting material does not affect the ultrasonic performance of the handpiece so that the potting material does not affect the longitudinal vibration of the piezoelectric stack.

2. The handpiece of claim 1 wherein the sleeve is polyetheretherketone.

3. The handpiece of claim 1 wherein the potting material is a primerless silicone adhesive.

* * * * *